United States Patent
Hufford et al.

(10) Patent No.: US 11,937,891 B2
(45) Date of Patent: Mar. 26, 2024

(54) SYSTEMS AND METHODS OF CONTROLLING SURGICAL ROBOTIC SYSTEM USING EYE-TRACKING

(71) Applicant: Asensus Surgical US, Inc., Durham, NC (US)

(72) Inventors: Kevin Andrew Hufford, Cary, NC (US); Nicholas J Bender, Raleigh, NC (US); Alexander John Maret, Apex, NC (US); Matthew Robert Penny, Holly Springs, NC (US); Paul Wilhelm Schnur, Pipersville, PA (US); Dustin Owen Vaughan, Raleigh, NC (US); Sevan Abashian, Morrisville, NC (US); Michael Okyen, Morrisville, NC (US)

(73) Assignee: Asensus Surgical US, Inc., Durham, NC (US)

( * ) Notice: Subject to any disclaimer, the term of this patent is extended or adjusted under 35 U.S.C. 154(b) by 284 days.

(21) Appl. No.: 17/064,222

(22) Filed: Oct. 6, 2020

(65) Prior Publication Data

US 2022/0104898 A1 Apr. 7, 2022

(51) Int. Cl.
*A61B 34/37* (2016.01)
*A61B 34/20* (2016.01)
*A61B 90/00* (2016.01)
*G06F 3/01* (2006.01)

(52) U.S. Cl.
CPC ............ *A61B 34/37* (2016.02); *A61B 34/20* (2016.02); *A61B 90/37* (2016.02); *G06F 3/013* (2013.01); *A61B 2034/2057* (2016.02); *A61B 2090/372* (2016.02)

(58) Field of Classification Search
CPC ......... A61B 34/37; A61B 34/20; A61B 90/37; A61B 2034/2057; A61B 2090/372; G06F 3/013
USPC ....................................................... 606/130
See application file for complete search history.

(56) References Cited

U.S. PATENT DOCUMENTS

| | | | | |
|---|---|---|---|---|
| 10,155,166 | B1 * | 12/2018 | Taylor | A63F 13/25 |
| 2011/0234630 | A1 * | 9/2011 | Batman | G16H 40/63 |
| | | | | 345/629 |
| 2017/0172675 | A1 * | 6/2017 | Jarc | A61B 90/361 |
| 2018/0128681 | A1 * | 5/2018 | Otsuka | A61B 5/489 |
| 2018/0200004 | A1 * | 7/2018 | Carnes | A61B 90/37 |

* cited by examiner

*Primary Examiner* — Mark Edwards

(57) ABSTRACT

A surgical robotic system includes at least one eye tracking system positioned detect the direction of at least one user's gaze. Input derived from the eye tracking system may be used to enter commands to the surgical robotic system depending on the directions of the gaze detected or other aspects of the gaze such as pupil dilation or speed of eye movement.

11 Claims, 4 Drawing Sheets

SYSTEMS AND METHODS OF CONTROLLING SURGICAL ROBOTIC SYSTEM USING EYE-TRACKING

BACKGROUND

US Published Application No. 2013/0030571 (the '571 application), which is owned by the owner of the present application and which is incorporated herein by reference, describes a robotic surgical system that includes an eye tracking system. The eye tracking system detects the direction of the surgeon's gaze and enters commands to the surgical system based on the detected direction of the gaze.

FIG. 1 is a schematic view of the prior art robotic surgery system 10 of the '571. The system 10 comprises at least one robot arm 11 which acts under the control of a control console 12 managed by the surgeon who may be seated at the console. The system includes multiple robotic arms 11. Three such arms are shown but a larger or smaller number may be used. Each robotic arm can support and operate a surgical instrument for use on a patient 13. One of the instruments is preferably a camera 14 which records the operating field inside the patient, while the other instruments may be known surgical tools 15, 16.

The arms 11 are operated by an electronic control unit 30 which causes the arms to perform the movements entered via the console 12. The unit 30 will receive the high-level movement commands (for example, desired position and inclination of the tool supported by the robot) and will execute them, converting them into the corresponding sequences of signals to be sent to the individual motors of the robot arm articulations. Other details of the system 10 are found in the '571 application which is fully incorporated herein by reference.

The console includes input devices 17, 18 which can be gripped by the surgeon and moved so as to deliver instructions to the system as to the desired movement and operation of the instruments supported by the arms 11. The surgeon's movements are suitably reproduced by the surgical instruments by means of movement of the robot arms 11. The input devices may be equipped to provide the surgeon with tactile feedback so that the surgeon can feel on the input devices 17, 18 the forces exerted by the instruments on the patient's tissues.

Each input device will typically operate a robot arm. The '571 application describes that where there are more than two arms, the system includes a control on the console that allows the surgeon to assign each arm to a desired instrument. The console may also include a keyboard 19 and/or touch screen and/or other command input devices. These other command devices might include a pedal device 20, and a button(s) on or in proximity to one or both handles of the input devices 17, 18.

The console 12 has an eye movement tracking system 21 or so-called "eye tracker" for detecting the direction of the surgeon's gaze towards the console and for controlling the surgical system depending on the gaze directions detected. In this way, the surgeon may control functions of the system by means of movement of his/her eyes.

The console also includes a video screen 22 with at least one zone 23 for showing a view of the operating field as captured by the camera 14, as well as other zones 29 that can provide other information to the surgeon and/or give the surgeon selectable options for control of some aspect of the system. The screen 22 may provide two-dimensional viewing, or stereoscopic/3D viewing. In the latter case, the surgeon may wear 3D viewing glasses 28 while observing the images captured on the screen.

The tracking system 21 detects the direction of the surgeon's gaze towards the screen 22 and defines which zone of the screen he/she is looking at or not looking at. The '571 discusses various uses for the tracking system. One example includes use of the tracking system to send a command which disables the movement of the robot arms when the system detects that the direction of the surgeon's gaze falls outside of the screen, or at least outside the screen zone which reproduces the operating field. As another example, the computerized system 24 displays on the screen 22 selectable zones 29 that form part of the human machine interface, allowing the surgeon to select a command by directing his/her gaze towards the one of the zones 29 that is associated with that command. The tracking system estimates the direction of the surgeon's gaze and performs selection of the commands associated with a zone when it detects a gaze direction which falls within this zone. In one particular example described in the '571, the commands associated with the selection areas 29 comprise the commands for assigning particular ones of the arms to the input devices. That allows the surgeon to alternate control of the robot arms on the two input devices without letting go of the input devices, but instead by simply looking at the corresponding selection areas on the screen. For example, the surgeon may temporarily switch one input device 17, 18 over to control of the arm with the camera, in order to modify the view of the operating field. Once the camera has been moved, the surgeon can rapidly re-assign that input device to the robot arm s/he had previously been. These steps can be performed by using the eye tracking features to "drag and drop" icons on the console display towards icons representing the various arms.

The '571 also describes use of the eye tracker to detect the distance between the screen and surgeon's eyes as a way to allow the surgeon to "zoom" the camera display in or out. The system enlarges the picture of the operating field shown on the screen depending on a variation in the distance detected. With this feature, the surgeon can intuitively perform enlargement of the picture by simply moving his/her face towards the screen and, vice versa, increase the viewing area of the operating field, thus reducing enlargement, by moving his/her face away from the screen.

Another application for the gaze tracking system described in the '571 is the control of movement of the camera mounted on one of the arms. When this function is enabled (e.g. by entering an input command, such as through pressing of a button on the console, depressing a foot pedal, etc), the movement of the eyes over the image of the operating field on the screen causes the movement of the robot arm supporting the camera. This can be used to place the zone the surgeon focused on at the center of the display screen The present application describes various implementations of eye tracking systems for robotic surgical procedures as well as various uses for eye input.

DESCRIPTION

Figure 1:
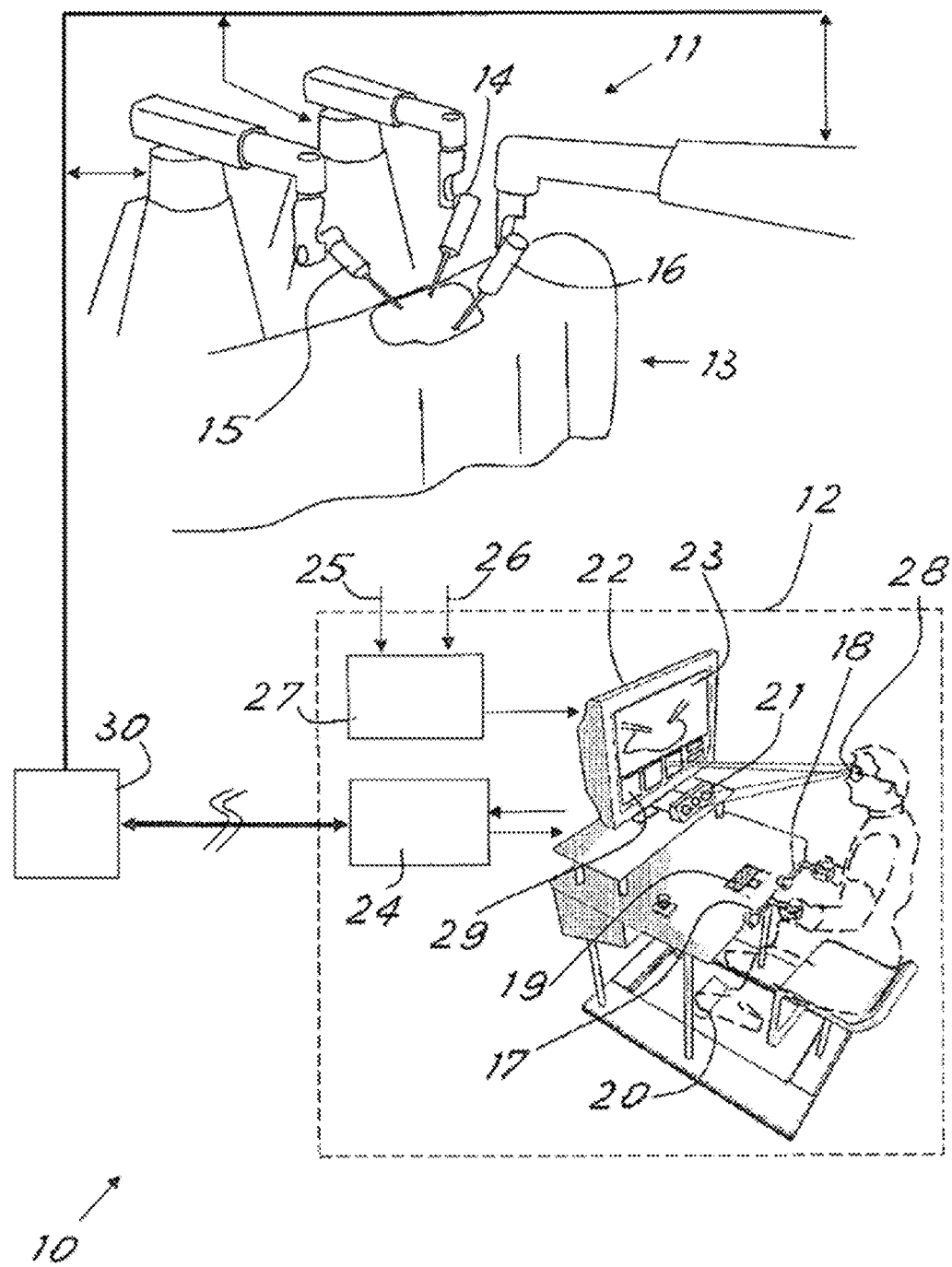
FIG. 1 shows an exemplary surgical system with which the embodiments described herein may be used.

Described below are various arrangements of eye tracking systems for robotic surgical procedures as well as various ways in which eye input can be used in surgical procedures. These arrangements and procedures can make use of eye trackers of the type disclosed in the '571, and reference is made to FIG. 1 (which shows the '571 system) to identify basic components of the '571 system that are also present in the new embodiments described here. It should be appreciated, though, that eye trackers other than those described in the '571 may be used for the described embodiments. Moreover, since eye trackers are known to those skilled in the art, particular details of eye trackers are not given.

The embodiments described herein may be used with a robotic system of the type disclosed in the '571, or other robotic systems.

The embodiments that are described might use eye tracking devices of the type described in the '571 application, and/or eye tracking devices that may be worn on the head. Examples of head mountable eye tracking devices include eye tracking glasses (such as eye tracking devices commercially available from Tobii AB www.tobii.com). See, for example, US Patent Application 2015/0061996, entitled "Portable Eye Tracking Device" owned by Tobii Technology AB and incorporated herein by reference. In some embodiments, eye tracking features may be incorporated into the glasses 28 (FIG. 1) worn by surgical personnel when viewing the 3-dimensional display from the camera. For other applications for such devices, see commonly owned U.S. Ser. No. 17/064,334, entitled Surgeon Interfaces using Augmented Reality, filed on the same day as the present application and incorporated herein by reference.

In a first embodiment, a robotic surgical system is provided with eye tracking devices positioned to track eye movements of multiple users (surgeons and surgical staff) within the operating room. In the example shown in FIG. 2, the surgeon console 12 includes an eye tracker as described with respect to FIG. 1 for the surgeon 20 seated at the console, and one or more additional eye trackers 21a, 21b positioned in proximity to additional screens 22a, 22b that are oriented for viewing by one or more additional surgical personnel 20a, 20b. The trackers 21a, 21b may be integrated with the screens 22a, 22b or separate components. The trackers 21a, 21b may be configured so that during use each one tracks eye movement of a particular one of the user 20, 20a, 20b. Alternatively, the system may be set-up to distinguish between users and/or it may be set up such that a particular tracker will track eye movement of a particular one of the users upon receiving a particular command from an auxiliary input (e.g. a voice command, or input from a wireless device or other type of input device) signaling that eye movement commands should be read for a particular user. In this type of embodiment, a single one of the eye trackers 21a, 21b can thus be used by multiple ones of the users 20a, 20b to input commands to the system. In yet another modification to the first embodiment, the eye trackers 21, 21a, 21b are incorporated into glasses (see glasses 28 of FIG. 1) worn by the users 20, 20a, 20b. The first embodiment and the variations thereof may be configured to allow users to collaborate on the features/controls provided by eye tracking.

Figure 2:
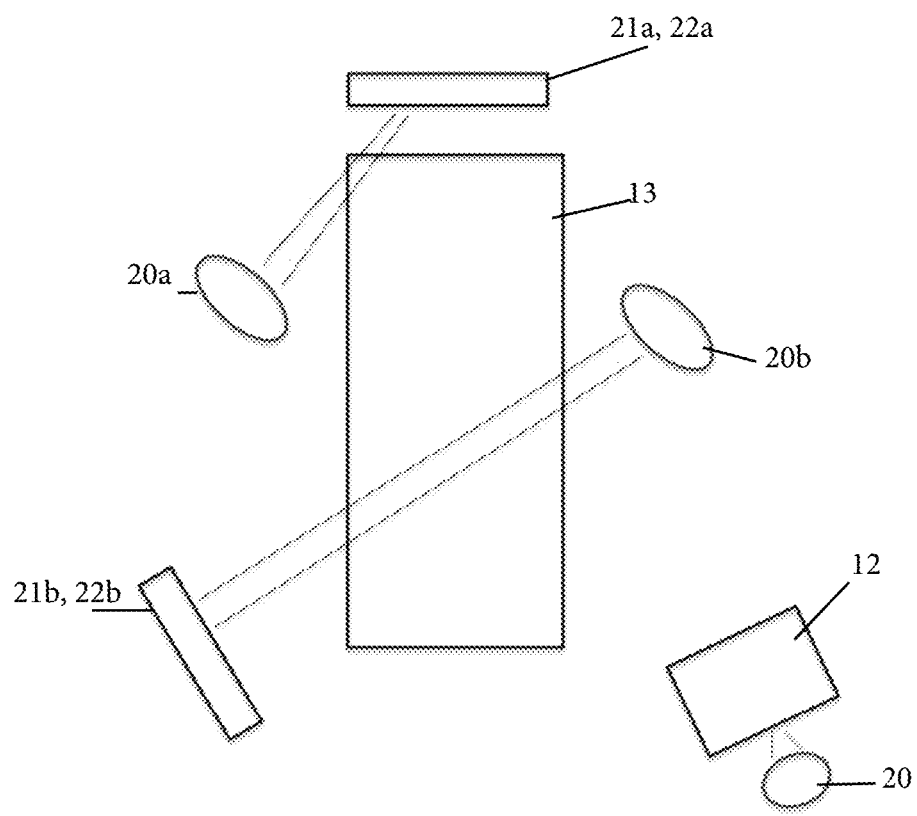
FIG. 2 schematically illustrates positioning of users and eye trackers in accordance with a first embodiment.
Figure 3:
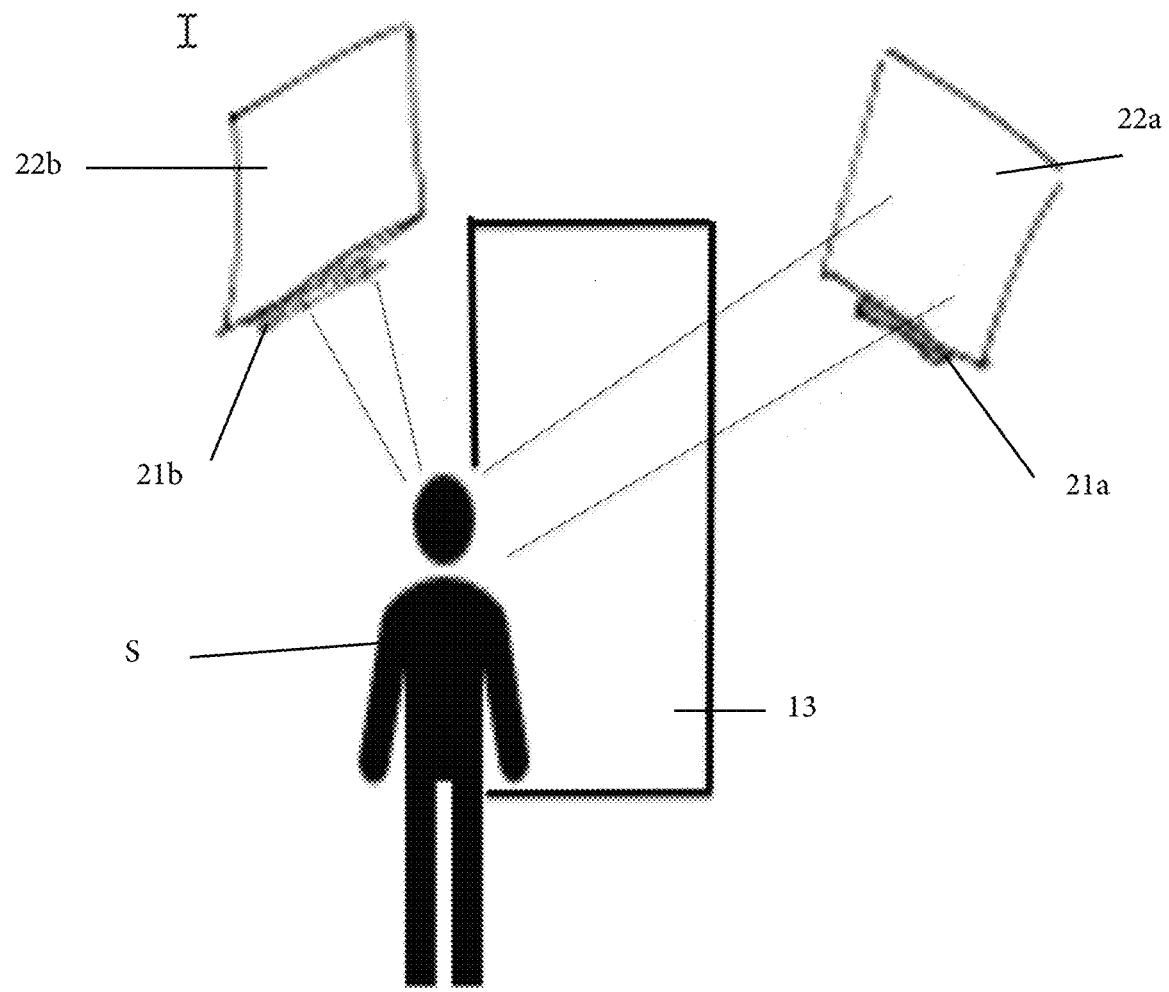
FIG. 3 schematically illustrates positioning of users and eye trackers in accordance with a second embodiment.

In a second embodiment, multiple eye trackers 21a, 21b are set up within the operating room in a manner similar to that shown in FIG. 2, but they are oriented so that a surgeon 20 or other user whose gaze is being tracked can look at various locations within the operating room (e.g. at multiple monitors 22a, 22b within the operating room) while still being able to have his/her eyes tracked. See FIG. 3. This enables the user to view multiple monitors in the operating room, such as the primary display at the surgeon console as well as other monitors in the operating room (such as those that display the surgical field to other operating room personnel) while maintaining eye tracking control of features of the robotic surgical system.

Figure 4:
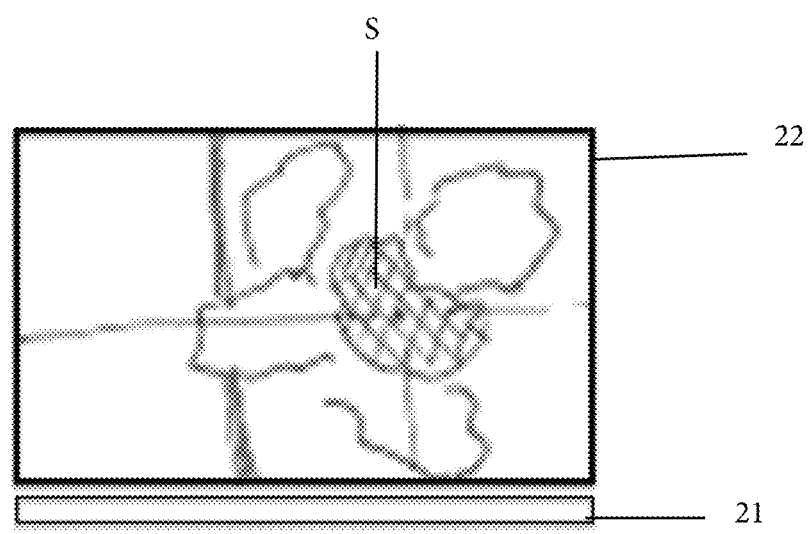
FIG. 4 illustrates an image display and illustrates use of eye tracking to mark regions of interest.

A third embodiment, illustrated in FIG. 4, is an exemplary application for an eye tracking system, where input from the eye tracker causes anatomical features or regions of interest to the surgeon to be marked on the camera display 22 using indicia, coloring, highlighting, text or other indicating features. The computer system 24 system is programmed such that as the surgeon views the camera display 22, the eye tracking system detects where on the display the surgeon is looking (represented by the intersection of perpendicular lines in FIG. 4), and the system 24 causes markings, text, or other indicating features S to be added to the surgical display and/or enhances the image at the user's focus point. This might be done to call out those features to others present in the operating room or to allow a record of, or information about, such features to be preserved on a recording of the image.

The cue to the system to mark the location or region on the image at which the user is gazing may be input to the system using some form of auxiliary user input device, such as one that detects voice commands, blinking/winking by the surgeon, input from a button (e.g. on the input handle 17, 18 or foot pedal 20), a touch input etc. The surgeon console might additionally or instead use auxiliary input devices that detect EEG or brain activity as indicators of when the surgeon is viewing a region s/he considers sufficiently important to be marked. This allows the system to be configured to detect a certain form of brain activity, or activity exceeding a certain threshold, and to then mark the display once that form/level of activity is detected. Myoelectric sensors could be positioned on the surgeon's skin, such as the forehead, allowing muscle movement (e.g. raising of eyebrows) to instead be used to give input to the system that the region at which the surgeon is looking should be marked.

Note that where blinking/winking is used as auxiliary input, the eye tracking system detects the absence of a gaze for a certain period of time. Blinking/winking may be used as eye input for certain functions of the system, including as auxiliary input in the various embodiments described above.

Returning again to FIG. 4, the indicating features added to the display are in the form of shading S over a region of the display corresponding to the area of the surgeon's focus. The system 24 might be configured so that, as the user moves his or her gaze from a first region of the display to a second region of the display, the input from the eye tracker is used by the system to cause the system to enhance the image in that region of the camera display—so in the FIG. 4 embodiment shading S would be removed from the region shown in FIG. 4 and added in the second region. The system may be programmed such that the image is processed to highlight as much of the specific anatomical feature as desired. For example, where the visualization system is one capable of determining tissue topography, the system might be programmed to highlight all tissue at a common depth to that at which the surgeon is gazing, or the camera might be caused to focus to the depth of the tissue that the surgeon is looking at. Alternatively, where the visualization system is one capable of distinguishing blood vessels from surrounding tissue, the system might be programmed to highlight the full length (or the length present within the visual field) of a blood vessel at which the surgeon is looking. This may, for example, show the image of the vessel with fluorescence imaging in a local region surrounding the focus of the surgeon's gaze while leaving a standard image for the rest of the surgical display.

In some cases, it might be desirable to monitor the surgeon's stress level during a surgical procedure or during training. A fourth embodiment makes use of an eye tracking system to monitor the surgeon's stress level, such as by detecting pupil dilation changes or eye motion speed changes, which can be used as metrics of stress. In such systems, such parameters detected by the eye tracking system may be considered in conjunction with other signals detected from other supplemental sensors to provide a more comprehensive characterization of stress or focus level. Supplemental sensors might include those that detect galvanic skin response, heart rate, respiratory rate, EEG, or other physiological or behavioral metrics. Some of this input may be generated using supplemental sensors on the user input handles (e.g. for measuring heart rate using electrodes or optical detection, and perspiration rate through galvanic skin response detection). The robotic system can determine when the eye tracking input and other supplemental sensor input indicates a heightened stress level by the surgeon, and then modify the parameters of the control system of the robot or the control mode of the robot to optimize usability for high focus or stressful tasks. For example, the system might switch to a mode in which hand tremor filtration is added or enhanced, or it might switch to a mode in which the surgical instruments move more slowly relative to the speed of input device motion (lower scaling factor).

In addition, eye tracking may be used to monitor the surgeon's focus or attentiveness, prompting the system to change into a safer mode of operation or to impose greater rate limitations on instrument movement, etc when the robotic system determines that the surgeon's focus or attentiveness has decreased or fallen below and predetermined threshold. One example of a safer mode would be one using an altered scaling factor so the instruments move more slowly relative to the speed of the input handles than they would normally be caused to move. As another example, attentiveness measurements might function as a "deadman's switch" or a clutch that disables surgeon control of the system in the event surgeon attention is lost or greatly diminished.

In other applications, menus of information such as (a) available control modes or motions for elements of the robotic systems; (b) inventories of instruments that have been used thus far in the procedure and those that remain available for use, (c) procedure information such as real-time patent physiologic data, pre-procedure notes, procedure time, might be displayed on a monitor 22, smart glasses, or other HUD (heads up display). The user can gaze at a menu option on the display and select the item that s/he wants to review by delivering input to the system via auxiliary input such as voice command, input button, foot pedal, gesture, or other method. The system uses the eye gaze tracking to determine which menu option the surgeon was looking at when s/he delivered the auxiliary input, and then displays the corresponding information. Changes in control modes may be achieved using this feature. For example, a user might look to an icon on the screen representing the scaling factor used for the instruments, give the auxiliary input to inform the system that the scaling factor is to be changed, and then give further input (e.g. the movement of a switch, rolling of a dial, foot pedal actuation, or other input modalities known in the art) to give the input to make the change in the scaling factor.

Another application for eye tracking allows the user to "swipe" a screen in a manner similar to that in which a smart phone allows a user to swipe between images, pages, applications, etc. In this embodiment, the eye tracking system 21 tracks the user's rapid eye movements across the screen, either horizontally or vertically, and uses this recognized gesture as input for a variety of actions. Actions that may be performed as a result of this eye movement might include, for example, changing between pages or images that are displayed to the user, selecting items from a menu, changing which instrument is to be actively controlled by a particular input device, dragging and dropping icons on the display, moving a robotic arm during surgical setup, setting camera views, controlling lighting of the surgical field, selecting camera settings, or triggering the recording of videos and images.

While certain embodiments have been described above, it should be understood that these embodiments are presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Moreover, features of the various disclosed embodiments may be combined in various ways to produce various additional embodiments.

Any and all patents, patent applications and printed publications referred to above, including for purposes of priority, are incorporated herein by reference.

We claim:

1. A surgical robotic system comprising:
a camera positionable at a surgical site within a body cavity to capture images of a surgical field;
at least one robotic arm configured to carry a surgical instrument, the surgical instrument maneuverable by the robotic system in accordance with input from a surgeon input device,
a camera display for displaying images of the surgical field captured by the camera, and
an eye tracking system positionable to detect the direction of a gaze of a user towards the camera display,
wherein the system is configured to distinguish blood vessels from surrounding tissue in the camera images and to, in response to detection of the user's gaze towards a blood vessel in an image that is displayed on the display, add indicia to the displayed camera images, the indicia overlaying a first region of the image comprising both a first portion at which the user's gaze meets the camera display and a second portion that is displayed on the camera display but is outside the first portion, to highlight a full length of the blood vessel visible on the camera display as said full length to differentiate said full length from the surrounding tissue.

2. The system of claim 1, wherein the indicia are selected from indicia including shading, coloring, outlining, highlighting, text, graphics, or other images.

3. The system of claim 2, wherein the system is configured to, in response to movement of the gaze to a second region on the display, adding indicia to the second region.

4. The system of claim 1, wherein the indicia is added to the first region in response to detection of auxiliary input to the system.

5. The system of claim 4, wherein the auxiliary input is selected from a group consisting of a visual cue, verbal command, button press, brain activity input or myoelectric input.

6. The system of claim 1, wherein the indicia comprise text dictated by surgical personnel about the region.

7. A system comprising:
   a camera positionable at a surgical site within a body cavity to capture images of the surgical site;
   a display for displaying images of the surgical site captured by the camera; and
   an eye tracking system positionable to detect the direction of a gaze of a user towards the display,
   wherein the system is configured to distinguish blood vessels from surrounding tissue in the camera images and to, in response to detection of the user's gaze towards a blood vessel in an image that is displayed on the display, add indicia to the displayed camera images, the indicia overlaying a first region of the image comprising both a first portion at which the user's gaze meets the camera display and a second portion that is displayed on the camera display but is outside the first portion, to highlight a full length of the blood vessel visible on the camera display to differentiate said full length from the surrounding tissue.

8. The system of claim 7, wherein the indicia is added to the first region in response to detection of auxiliary input to the system.

9. The system of claim 3, wherein the indicia are selected from indicia including shading, coloring, outlining, highlighting, text, graphics, or other images.

10. The system of claim 7, wherein the indicia comprise text dictated by surgical personnel about the region.

11. The system of claim 7, wherein the auxiliary input is selected from a group consisting of a visual cue, verbal command, button press, brain activity input or myoelectric input.

* * * * *